United States Patent
Wade et al.

(10) Patent No.: US 11,211,788 B2
(45) Date of Patent: Dec. 28, 2021

(54) FIRE RISK MITIGATION IN ELECTRIC POWER SYSTEMS

(71) Applicant: Schweitzer Engineering Laboratories, Inc., Pullman, WA (US)

(72) Inventors: Austin Edward Wade, Moscow, ID (US); Krishnanjan Gubba Ravikumar, Pullman, WA (US)

(73) Assignee: Schweitzer Engineering Laboratories, Inc., Pullman, WA (US)

( * ) Notice: Subject to any disclaimer, the term of this patent is extended or adjusted under 35 U.S.C. 154(b) by 52 days.

(21) Appl. No.: 16/800,062

(22) Filed: Feb. 25, 2020

(65) Prior Publication Data

US 2021/0265834 A1 Aug. 26, 2021

(51) Int. Cl.
*H02M 7/26* (2006.01)
*H02H 7/26* (2006.01)
(Continued)

(52) U.S. Cl.
CPC ......... *H02H 7/263* (2013.01); *G01N 33/0036* (2013.01); *G01P 13/00* (2013.01); *G01P 15/00* (2013.01); *G01R 19/16571* (2013.01); *G01R 31/085* (2013.01); *G08C 19/00* (2013.01); *H02H 1/0007* (2013.01); *H02H 7/265* (2013.01)

(58) Field of Classification Search
CPC ...... H02H 7/263; H02H 7/265; H02H 1/0007; G08C 19/00; G01N 33/0036
See application file for complete search history.

(56) References Cited

U.S. PATENT DOCUMENTS

| 4,635,055 A | 1/1987 | Fernandes |
| 6,205,867 B1 | 3/2001 | Hayes |

(Continued)

FOREIGN PATENT DOCUMENTS

| WO | 2006050156 | 5/2006 |
| WO | 2015087284 | 6/2015 |

OTHER PUBLICATIONS

ASTROSE® "Power Line Monitoring System for High Voltage and Extra High Voltage Power Lines" Fraunhofer-Institut für Zuverlässigkeit und Mikrointegration IZM, Oct. 2015.
(Continued)

*Primary Examiner* — Adolf D Berhane
*Assistant Examiner* — Afework S Demisse
(74) *Attorney, Agent, or Firm* — Gregory C. Baker; Phillips Winchester LLC (57) ABSTRACT

Systems and methods may mitigate risk of fire caused by an electric power system. In one embodiment, a system may include an intelligent electronic device (IED). The IED includes a communication subsystem to receive a signal from a sensor related to a condition of the electric conductor. A processing subsystem in communication with the communication subsystem may operate in at least two modes comprising a high security mode and a fire prevention mode. In the fire prevention mode, the IED may interrupt a flow of electric current based on the signal from the at least one sensor associated with the electric conductor. In the high security mode, the system may interrupt a flow of electric current based on the signal from the at least one sensor associated with the electric conductor and based on a second condition relating to the electric conductor.

19 Claims, 3 Drawing Sheets

(51) Int. Cl.
  *G08C 19/00* (2006.01)
  *G01R 19/165* (2006.01)
  *G01P 13/00* (2006.01)
  *G01N 33/00* (2006.01)
  *G01R 31/08* (2020.01)
  *H02H 1/00* (2006.01)
  *G01P 15/00* (2006.01)

(56) References Cited

U.S. PATENT DOCUMENTS

| | | |
|---|---|---|
| 8,738,318 B2 | 5/2014 | Spillane |
| 9,372,172 B2 | 6/2016 | Cheng |
| 9,562,925 B2 | 2/2017 | Nulty |
| 9,753,080 B2 | 9/2017 | Andle |
| 2006/0125469 A1 | 6/2006 | Hansen |
| 2009/0243876 A1 | 10/2009 | Lilien |
| 2012/0029871 A1 | 2/2012 | Spillane |
| 2012/0173146 A1 | 7/2012 | Mohr |
| 2013/0054162 A1 | 2/2013 | Smith |
| 2013/0205900 A1 | 8/2013 | Nulty |
| 2014/0123750 A1 | 5/2014 | Liu |
| 2014/0136140 A1 | 5/2014 | Chan |
| 2014/0266237 A1 | 9/2014 | Lindsey |
| 2016/0084893 A1* | 3/2016 | Gubba Ravikumar ............ G01R 21/00 702/60 |
| 2016/0329700 A1* | 11/2016 | O'Brien ............ H02H 3/48 |
| 2017/0227677 A1 | 8/2017 | Ampacimon |
| 2018/0238955 A1 | 8/2018 | Bango |
| 2018/0316219 A1 | 11/2018 | Bliss |
| 2019/0324074 A1 | 10/2019 | Thompson |
| 2020/0225273 A1 | 7/2020 | Manson |
| 2021/0091559 A1 | 3/2021 | Mobley |

OTHER PUBLICATIONS

TLM® Conductor Monitor "Real Time Transmission Line Conductor Monitor" Lindsey Manufacturing Company, Mar. 2017.

AE-150™ "PD & Hot Spots Detection and Localization System for Power Transformers" NBD Technologies Inc., Feb. 2017.

Pabuna, Eduardo "Substation Surveillance Using Radio Frequency Interference (RFI) Measurements", Westco Electrical, Nov. 2014.

Guo, Geng, et al. "Energy Harvesting Devices for High Voltage Transmission Line Monitoring", 2011 IEEE Power and Energy Society General Meeting, Jul. 2011.

Janus, Patrick "Acoustic Emission Properties of Partial Discharges in the Time-Domain and their Applications" 2012.

PCT/US21/16791 International Search Report and Written Opinion of the International Searching Authority, dated Apr. 20, 2021.

* cited by examiner

FIRE RISK MITIGATION IN ELECTRIC POWER SYSTEMS

TECHNICAL FIELD

This disclosure relates to systems and methods for mitigating fire risk in electric power systems. More specifically, but not exclusively, the present disclosure relates to detection of damaged, broken, and/or downed electric power lines and monitoring of environmental conditions to implement additional safety precautions to mitigate risk of fire.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Electric power systems commonly use various components (e.g., conductors suspended between pylons) to transmit and distribute electric power. Components of the electric power system may be damaged by a wide variety of circumstances ranging from weather, to traffic accidents, to vandalism, etc. For example, damaged, broken, or downed electric conductors, or other components of the power distribution network, may cause fires, other hazardous conditions, and disrupted electric service. Accordingly, the detection of a fault may reduce risk to persons and property and may reduce the likelihood of or even substantially prevent fires caused by the conductor. Further, the detection of a faulted electric conductor may be an initial and necessary step in ultimately assessing the fault and repairing the electric power system.

Identifying faults (e.g., arcing, high-impedance faults (HIF), etc.) in electric system components may be especially critical during times of high fire risks (e.g., to prevent wildfires). Wildfires caused by electric utilities caused over $15 billion dollars in damage in 2018 alone. In order to prevent future incidents, utility companies may cut power to large numbers of customers during high fire risk periods.

Systems and methods consistent with embodiments of the present disclosure may use detection methods, along with associated systems and methodology, to monitor risk levels (e.g., fire risk levels) and to take appropriate actions to monitor and control an affected power system. Wildfire danger is generally determined using relative humidity, windspeed, and fuel loads (e.g., amount of combustible vegetation determined by previous season weather and precipitation). Systems and methods consistent with embodiments of the present disclosure may implement data relating to one or more of the above indicators for wildfire danger when taking action on an affect power system.

In some embodiments, monitoring may include detecting broken or downed conductors that are typically suspended between two pylons in an electric power system. Such detectors may monitor the orientation of the device and may determine whether the conductor is damaged, broken, or downed based on the orientation of the device. Such detectors are discussed in detail in, for example, U.S. Patent Application Publication US 2019/0324074 A1, filed Apr. 20, 2018, the disclosure of which is incorporated in its entirety by this reference.

Embodiments consistent with the present disclosure may include sensors (e.g., distributed conductor sensors) along with environmental sensing and/or monitoring (e.g., fire risk monitoring and/or sensing). Such systems may assist in the reduction of the number of wildfires caused by electric power equipment. For example, the system may be configured to react when a fault is detected (e.g., by tripping a portion of the electric power system after detection of a damaged, falling, and/or broken conductor). The system may also proactively monitor and report conditions that are relevant to fault detection. The system may proactively monitor and report environmental conditions (e.g., back to a substation and/or control center) enabling for adaptive protection schemes (e.g., in time periods and/or locations experiencing a high fire risk) and/or appropriate actions to be taken in response to one or more apparent fault detections. For example, the system may use data from local weather and/or firefighting forecasts to determine fire risk and may take such data in account when reacting to an apparent fault condition. In additional embodiments, the system may directly measure the environmental conditions (e.g., with one or more sensors on electric conductors).

Various modes may be enabled to adjust an electric power system to the risk of fire based on conditions. For example, in some embodiments consistent with the present disclosure, a system may operate in a high security or high confidence mode. In this mode, multiple criteria may be used to evaluate whether a fault has occurred prior to deenergizing an associated conductor. Such a system may use a combination of detection of motion (e.g., acceleration) in the conductor and change in electrical conditions (e.g., a change in current) to substantially ensure that a conductor is actually damaged and is not providing a false positive indication of a fault. For example, when the conductor may be moving due to a galloping event and/or due to a line strike that has not caused the conductor to come into contact with adjoining objects, surfaces, and/or structures, an indication of motion alone may not provide enough certainty that remedial actions need to be taken (e.g., where such action may cause an undesirable power disruption). In some embodiments, other properties may be used to determine a fault in the conductor. For example, one or more sensors may monitor the conductor for a traveling wave to determine a fault in the conductor line.

In a fire prevention mode, the level of certainty required to interrupt power flowing through a conductor may be reduced or even eliminated if the risks associated with a fault are of a sufficient magnitude of concern (e.g., during a period and/or locale of high fire risk).

In the event that a fault is determined with a required level of certainty, the sensor may send a communication (e.g., in a mirrored bit configuration) to a control location (e.g., a substation) to trip and deenergize a portion of the power system or line (e.g., prior to the line hitting the ground). However, as discussed above, motion detection (e.g., accelerometer data) alone may not be secure enough (e.g., may not rise to a high enough level of certainty to disrupt power service in a selected locale) to determine an actual failing conductor or conductors as galloping conductors or line strikes may cause similar sensor readings, leading to a false positive condition. In some situations (e.g., a high security mode), additional data may be considered (e.g., changes in current, environmental conditions, etc.) before deenergizing part of an electric system in order to avoid unnecessary interruptions of service. In additional situations, where there is increased risk of harm due to a fault (e.g., a high fire danger mode, people near the affected the location, service personnel working on the power system, etc.) tripping without additional data or factors (e.g., during times of low relative humidity and/or during other forecasts identifying high fire danger) may be implemented for a length of time.

In some embodiments, a control system may use the information generated by one or more fault detectors (e.g., for detecting damaged, broken, or downed conductor detectors) to identify an appropriate control strategy in response to the fault. For example, a faulted conductor may be deenergized by the control system to reduce the risk of injury to persons and property and/or the risk of fire in the vicinity of the faulted conductor. The identification of a faulted power line may be used to minimize the disruption of electric service by permitting identification of the smallest possible area of the electric power system to be deenergized due to the faulty conductor.

In some electric power systems, multiple reclose operations (i.e., attempts to reenergize a power line) may be made following a trip to address transient conditions (e.g., a fault caused by a temporary gust of wind or animal contact). In various embodiments consistent with the present disclosure reclose operations may be blocked at time of high fire risk. Reclose operations may result in electric arcing, which could cause a fire, or create other types of hazardous conditions. While reclose operations may increase the reliability of an electric power system and reduce the costs of inspecting and clearing transient faults, under typical environmental conditions, such benefits may be outweighed by the risk associated with fire when the environmental conditions generate a high risk of fire (e.g., high winds, low humidity, etc.).

The embodiments of the disclosure will be best understood by reference to the drawings. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor do the steps need be executed only once, unless otherwise specified.

In some cases, well-known features, structures, or operations are not shown or described in detail. Furthermore, the described features, structures, or operations may be combined in any suitable manner in one or more embodiments. It will also be readily understood that the components of the embodiments, as generally described and illustrated in the figures herein, could be arranged and designed in a wide variety of different configurations. For example, throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Several aspects of the embodiments disclosed herein may be implemented as software modules or components. As used herein, a software module or component may include any type of computer instruction or computer executable code located within a memory device that is operable in conjunction with appropriate hardware to implement the programmed instructions. A software module or component may, for instance, comprise one or more physical or logical blocks of computer instructions, which may be organized as a routine, program, object, component, data structure, etc., that performs one or more tasks or implements particular abstract data types.

In certain embodiments, a particular software module or component may comprise disparate instructions stored in different locations of a memory device, which together implement the described functionality of the module. Indeed, a module or component may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules or components may be located in local and/or remote memory storage devices. In addition, data being tied or rendered together in a database record may be resident in the same memory device, or across several memory devices, and may be linked together in fields of a record in a database across a network.

Embodiments may be provided as a computer program product including a non-transitory machine-readable medium having stored thereon instructions that may be used to program a computer or other electronic device to perform processes described herein. The non-transitory machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions. In some embodiments, the computer or other electronic device may include a processing device such as a microprocessor, microcontroller, logic circuitry, or the like. The processing device may further include one or more special purpose processing devices such as an application specific interface circuit (ASIC), PAL, PLA, PLD, field programmable gate array (FPGA), or any other customizable or programmable device.

Electric power generation and delivery systems are designed to generate, transmit, and distribute electric energy to loads. Electric power generation and delivery systems may include equipment, such as electric generators, electric motors, power transformers, power transmission and distribution lines, circuit breakers, switches, buses, transmission lines, voltage regulators, capacitor banks, and the like. Such equipment may be monitored, controlled, automated, and/or protected using one or more control systems (e.g., central, remote, and/or local control systems) that may include intelligent electronic devices (IEDs) that receive electric power system information from the equipment, make decisions based on the information, and provide monitoring, control, protection, and/or automation outputs to the equipment.

In some embodiments, portions of a control system (e.g., an IED) may refer to any microprocessor-based device that monitors, controls, automates, and/or protects monitored equipment within overall electric power system. Such devices may include, for example, remote terminal units, differential relays, distance relays, directional relays, feeder relays, overcurrent relays, voltage regulator controls, voltage relays, breaker failure relays, generator relays, motor relays, automation controllers, bay controllers, meters, recloser controls, communication processors, computing platforms, programmable logic controllers (PLCs), programmable automation controllers, input and output modules, governors, exciters, statcom controllers, static VAR compensator (SVC) controllers, on-load tap changer (OLTC) controllers, and the like. Further, in some embodiments, IEDs may be communicatively connected via a network that includes, for example, multiplexers, routers, hubs, gateways, firewalls, and/or switches to facilitate communications on the networks, each of which may also function as an IED. Networking and communication devices may also be integrated into an IED and/or be in communication with an IED. As used herein, an IED may include a single discrete IED or a system of multiple IEDs operating together.

Figure 1:
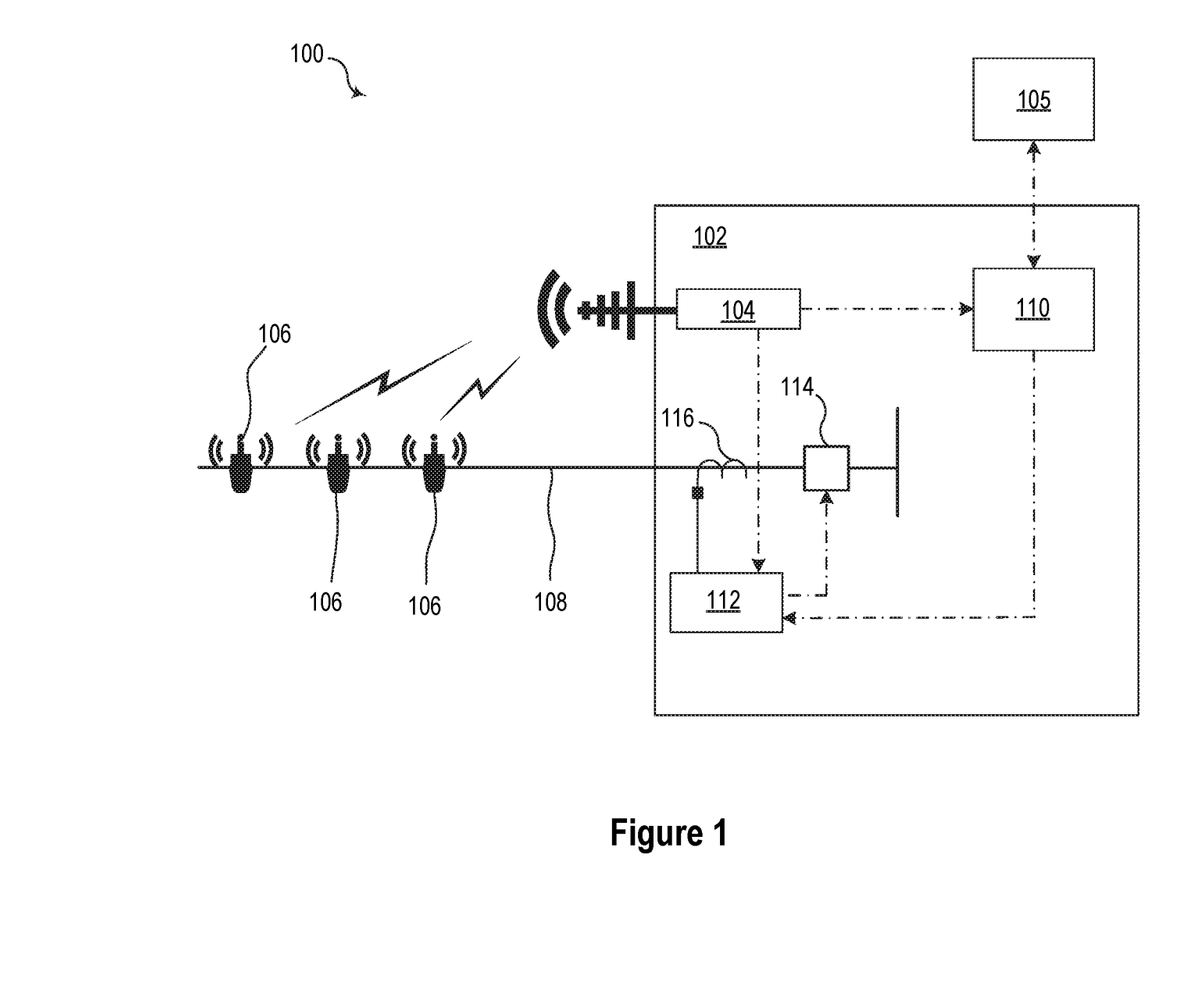
FIG. 1 illustrates an example of an embodiment of a simplified one-line diagram of a portion of an electric power delivery system in accordance with embodiments of the present disclosure.

FIG. 1 illustrates a simplified one-line diagram of a portion of an electric power transmission and distribution system. An electric power delivery system 100 or portion thereof may be monitored, controlled, automated, and/or protected using a monitoring system (e.g., a central monitoring system, a local monitoring system, such as, a substation 102, etc.). In general, such control systems including one or more IEDs in an electric power generation and transmission system 100 may be used for protection, control, automation, and/or monitoring of equipment in the system 100. For example, the system or components thereof may be used to monitor equipment of many types, including electric transmission lines, electric distribution lines, current transformers, busses, switches, circuit breakers, reclosers, transformers, autotransformers, tap changers, voltage regulators, capacitor banks, generators, motors, pumps, compressors, valves, and a variety of other types of monitored equipment.

In various embodiments, the substation 102 may be configured to monitor the frequency of alternating current waveforms, voltage levels, or other electric conditions in system 100. Communication subsystem 104 may be used to transmit information among various components in the system 100, including other control systems or IEDs. Communication subsystem 104 may operate using a variety of wired and/or wireless communication technologies. In various embodiments, the communication subsystem 104 may be configured to provide streaming measurements that may be analyzed consistent with the present disclosure to detect anomalies.

As depicted, the communication subsystem 104 may be in communication with a plurality of sensors 106 that communicate the status of one or more components of the electric power system 100 and/or environmental conditions. Sensors 106 may be positioned proximate (e.g., adjacent, on, coupled in, in communication with) one or more components of the electric power system 100 (e.g., electric conductor 108). Conductor 108 may be used to transmit and/or distribute power in system 100. A fault associated with conductor 108 may pose a risk to persons or property in proximity to system 100, along with increased fire danger. Timely detection and mitigation of a fault may reduce the risk of injury to persons or damage to property, reduce the risk of igniting of fire, and may assist to expedite restoration of electrical service.

As discussed above, the sensors 106 may monitor physical or electrical conditions associated with conductor 108 and/or environmental conditions. For example, the sensor 106 may detect movement of the conductors 108 and/or may detect anomalies in electrical conditions associated with conductors 108 (e.g., a spike in current). As also discussed above, the sensors 106 may monitor movement of the conductors 108 by monitoring one or more properties of the conductors 108 (e.g., position, rotation, rotational position, velocity, acceleration, impulse/jerk, etc.). Further, one or more ambient conditions (e.g., humidity, wind speed, temperature, etc.). In various embodiments, environmental conditions may include humidity measurements, temperature measurements, relative humidity measurements, fire danger forecasts, wind speed measurement or forecasts, combinations thereof, etc.

The communication subsystem 104 may be in further communication with other portions of the system 100 or remote components and/or systems that may communicate additional data relating to operation of the electric power system 100. For example, the communication subsystem 104 may receive one or more environmental conditions relating a location of the system 100 from one or more environmental data sources (e.g., a central control system 105, the sensor 106, an external source or database, etc.). The central control system 105 may be in communication directly with a controller 110 (as depicted) or may be in communication indirectly (e.g., through the communication subsystem 104). In some embodiments, the controller 110 may provide alarms and other data to the central control system 105.

The communication subsystem 104 may pass received data (e.g., relating to the status of one or more components the electric power system 100 and/or the environmental conditions) to the controller 110 (e.g., a processing subsystem). In some embodiments, the controller 110 may be at least partially or fully automated. For example, the controller 110 may act automatically (e.g., without intervention from a user) based on data received from the communication subsystem 104. In additional embodiments, user verification or intervention may be required before any actions are taken by the controller 110 (e.g., where a recommendation may be provided by the controller 110 to a user for verification of one or more actions).

The controller 110 may communicate with one or more control devices of the system 100 to deenergize one or more portions of the system 100. The controller 110 may communicate with a relay 112. Relay 112 may be in communication with a current sensor 116, which may provide a measure of current flowing through conductor 108. Relay 112 may use current sensor 116 to monitor for current surges, overcurrent conditions, or other electrical conditions indicative of a fault. Relay 112 may obtain additional electrical information from the conductor 108 such as voltage information. Relay 112 may monitor the conductor 108 to detect conditions for which the conductor 108 should be deenergized such as, for example, overcurrent, undercurrent, overvoltage, undervoltage, ground fault, and the like. The Relay 112 may detect one or more electrical traveling waves on the conductor 108 indicating a fault condition. As depicted, controller 110 may send a command to trip breaker 114 to interrupt current flow through conductor(s) 108.

The controller 110 may be configured to operate in one or more modes. The controller 110 may select (e.g., automatically select based on relevant data), or may be used to select (e.g., by a user), a first mode (e.g., a high security or high confidence mode) where multiple consistent criteria are required to be met to verify the occurrence of a fault before a trip command is sent to breaker 114. For example, in the high security mode, motion detected by one or more sensors 106 may be insufficient to trip breaker 114; however, if the motion corresponds to a current spike detected by current sensor 116, relay 112 may issue a command to breaker 114 to interrupt a current flow through conductor 108. In some embodiments, the high security mode may be the default operational mode for the system 100 or substation 102.

The controller 110 may select, or may be used to select, a second mode (e.g., a fire prevention mode) where multiple consistent criteria are not required to be met to verify the occurrence of a fault before a trip command is sent to breaker 114. For example, data from the sensors 106 (e.g., data relating to motion of the conductors 108) may not be required to be verified before a trip command is sent by relay 112. Rather, threshold data relating to the one or more environmental conditions (e.g., as discussed above) may instruct the controller 110 to bypass any verification and immediately trip to mitigate against the risk of igniting a fire. In some embodiments, threshold data relating to the one or more environmental conditions may automatically place the controller 110 in the fire prevention mode. In additional embodiments, the controller 110 may query the data relating to the one or more environmental conditions when a threshold event is received from the sensors 106 such that the controller 110 may determine which operation mode is appropriate and automatically take action or signal an operator to verify a proposed action or operational mode.

In some embodiments, in one or more modes of the substation 102, the communication subsystem 104 may bypass the controller 110 where a command received by the communication subsystem 104 may directly control the relay 112 (e.g., to cease power to or to reenergize the conductor 108. In such an embodiment, the controller 110 may instruct the relay 112 separately on actions to take (e.g., related to a selected mode) when data from the communication subsystem 104 is received directly at the relay 112.

Figure 2:
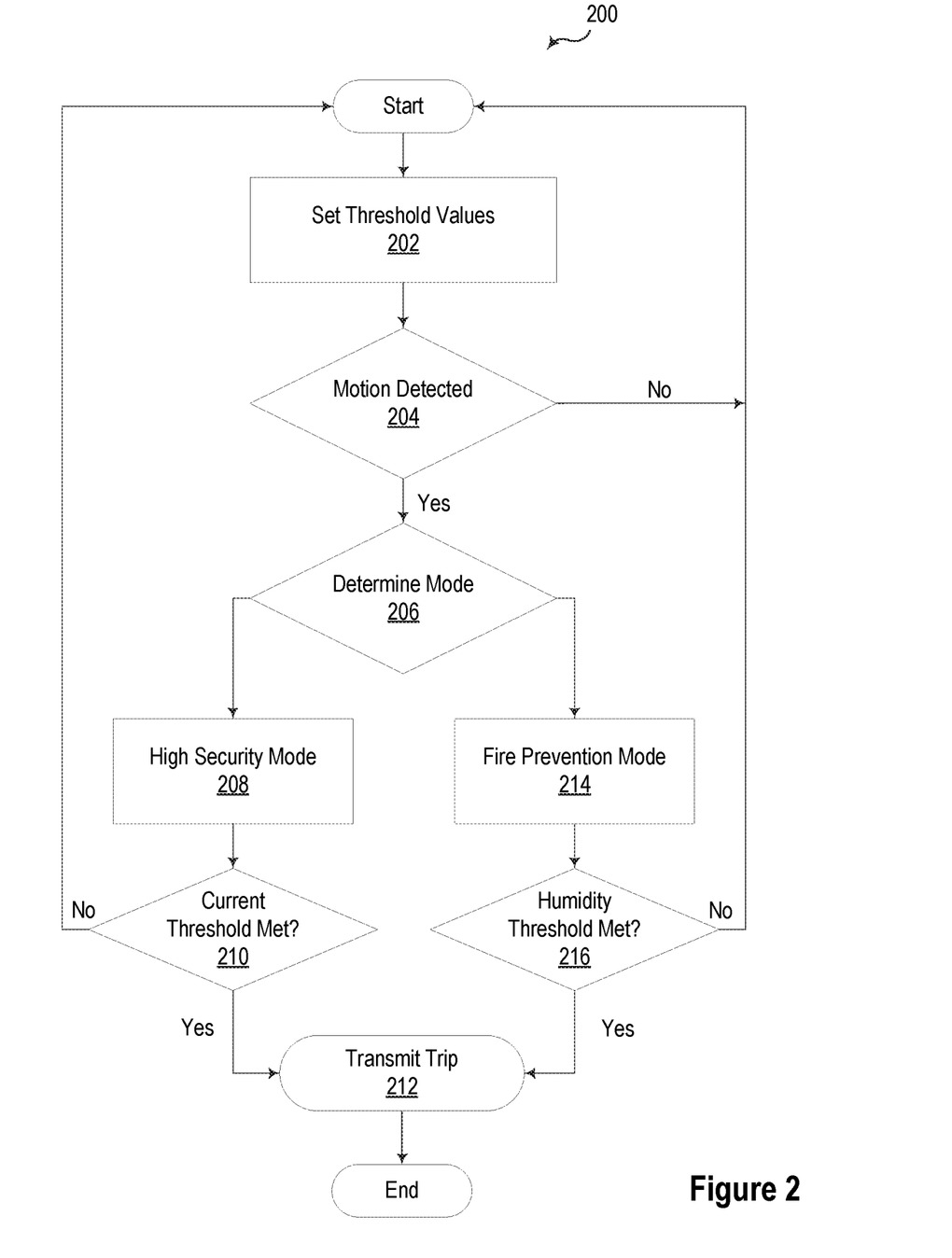
FIG. 2 illustrates a flow chart of a method for mitigating risk of fire in an electric power system in accordance with embodiments of the present disclosure.

FIG. 2 illustrates a flow chart of a method 200 for mitigating risk of fire in an electric power system in accordance with embodiments of the present disclosure. At 202, thresholds may be established for the control system, which thresholds may be optional after an initial setup. For example, the thresholds may dictate a threshold level of motion of a conductor, a threshold value of change in an electrical property of the electric transmission through the system (e.g., change in current), and/or a threshold environmental value (e.g., relative humidity, temperature, fire danger level, wind speed, etc.), where each threshold sets a value needed to be met or passed before action is taken.

At 204, data from the system (e.g., one or more sensors) is received to determine if a fault is present. For example, data from the sensors may indicate motion detected in one or more conductors. In some embodiments, the data from the sensor may be evaluated to determine if a traveling or standing wave is detected, as discussed above. If no motion is detected or the motion is determined to not be a fault (e.g., within a predetermined threshold level of certainty), no further action is taken.

At 206, a selected operational mode may be determined. As discussed, above, in some embodiments, the environmental data may automatically set the mode. Alternatively, the mode may be selected by an operator of an electric power system.

At 208, if a high security mode is detected, another verification beyond the detection of the motion is required.

At 210, data related to the further verification may be evaluated. For example, a current in the conductor may be compared to a threshold value (e.g., a predetermined current level, a previously detected current level, an average current level, etc., where each value may be modified by a selected percentage to arrive at the threshold value) to determine whether the current and/or change in current is within the set parameters.

If the current is within the parameters, method 200 may return to the start if the threshold values are to be redefined or updated or may return to 204 if the already set threshold values are maintained. If the current is not within the parameters (e.g., exceeds a threshold value), method 200 may proceed to 212 and may trip or deenergize part of the system (e.g., with an instantaneous overcurrent relay).

At 214, if a fire prevention mode is detected, the system may verify if an environment threshold is met. In additional embodiments, as discussed above, the environmental threshold being met may automatically place the system in the fire prevention mode and no further verification may be required before proceeding to trip or deenergize a portion of the system at 212.

At 216, data related to the environmental condition (e.g., humidity, relative humidity, temperature, wind speed, combustible material, etc.) may be evaluated. For example, a relative humidity may be compared to a threshold value (e.g., a predetermined relative humidity, etc.) to determine whether the relative humidity is above a set parameter. If the relative humidity is within the parameters, method 200 may return to the start if the threshold values are to be redefined or updated or may return to 204 if the already set threshold values are maintained. If the relative humidity is not within the parameters, method 200 may proceed to 212 and may trip or deenergize part of the system.

Figure 3:
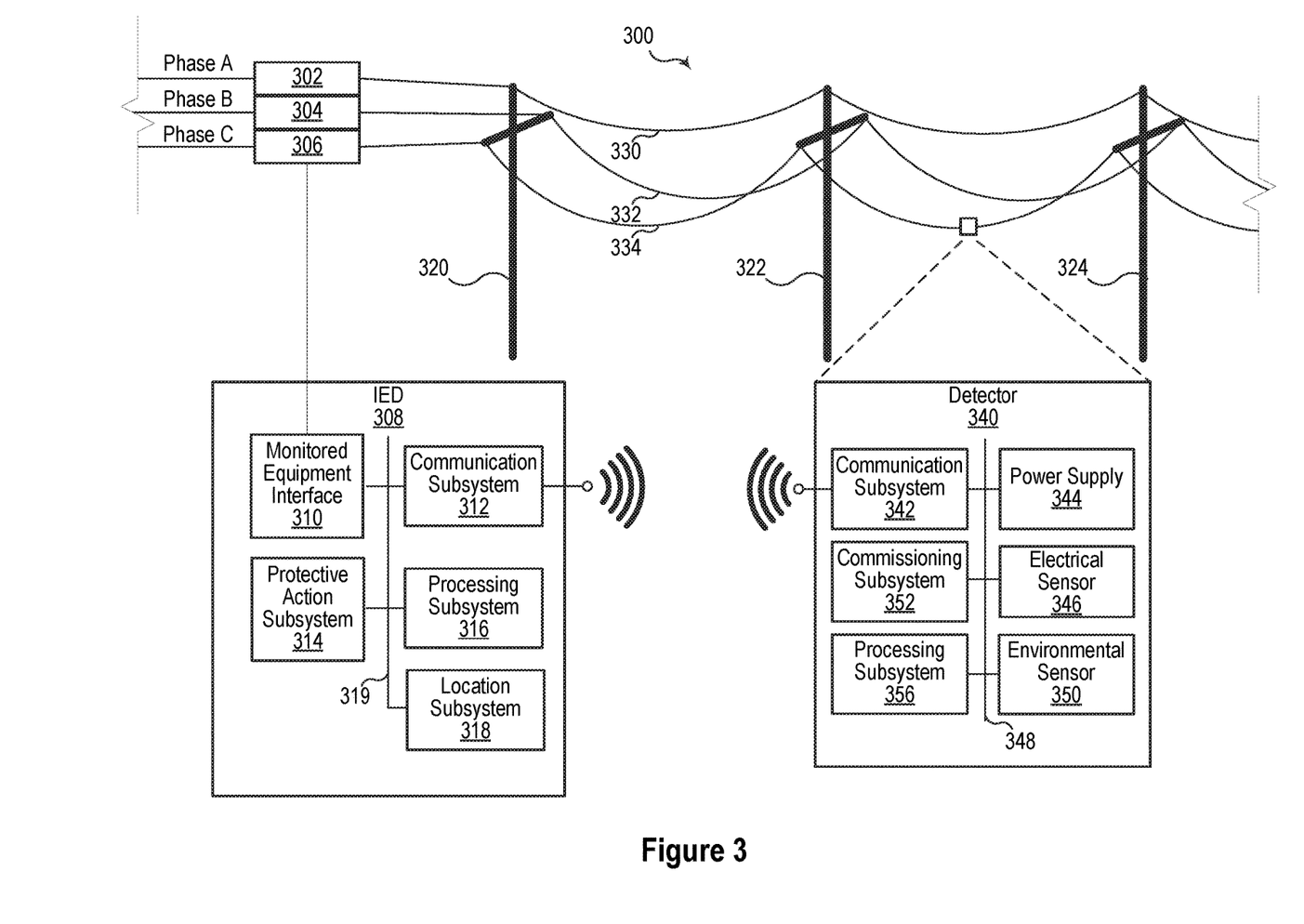
FIG. 3 illustrates a functional block diagram of a system to mitigate risk of fire in an electric power system in accordance with embodiments of the present disclosure.

FIG. 3 illustrates a functional block diagram of a system 300 comprising a line-mounted detector 340. System 300 may be implemented using hardware, software, firmware, and/or any combination thereof. In the illustrated embodiment, system 300 comprises a control system (e.g., substation) including an IED 308, while in other embodiments, certain components or functions described herein may be associated with other devices or performed by other devices. The specifically illustrated configuration is merely representative of one embodiment consistent with the present disclosure.

System 300 comprises conductors 330, 332, and 334, which are configured to transmit power. In various embodiments, the conductors may each be associated with a different electrical phase of a three-phase power system. In various other embodiments, the conductors may be the same phase of a poly-phase system. The conductors 330, 332, and 334 span the pylons 320, 322, and 324. Current interrupting devices 302, 304, and 306 may be in electric communication with the conductors 330, 332, and 334, respectively. In various embodiments, current interrupting devices 302, 304, and 306 may comprise devices to interrupt the flow of electrical current, such as reclosers, circuit breakers and the like. In some embodiments, current measuring devices (e.g., current transformers, Rogowski coils, and the like) may be associated with or encompassed by current interrupting devices 302, 304, and 306. In such embodiments, current measurements made by such devices may be used by system 300 to evaluate potential faults and determine whether system 100 should implement protective action.

IED 308 may be configured to monitor conductors 330, 332, and 334, and to implement protective actions to ensure the safe transmission of electric power. In various embodiments, IED 308 may receive information relating to electric conductions (e.g., current measurements, etc.) relating to electric conditions associated with conductors 330, 332, and 334. In addition, IED 308 may be in communication with a detector 340. IED 308 may implement protective action based on electric conditions and/or breakage of, for example, conductor 334. A single line-mounted sensor or detector 340 is shown on a single span of a single conductor 334 for purposes of simplicity in the illustrated embodiment. In other embodiments, a plurality of detectors (e.g., a distributed group of detectors 340) may be placed on each of conductors 330, 332, and 334 and on multiple spans between pylons 320, 322, and 324.

IED 308 may include a monitored equipment interface 310, a communication subsystem 312, a protective action subsystem 314, a processing subsystem 316, and a location subsystem 318. A bus 319 may connect the internal elements of IED 308. The monitored equipment interface 310 may be configured to issue commands to and/or receive status information from current interrupting devices 302, 304, and 306. Communication subsystem 312 may be configured to receive information from detector 340. In the illustrated embodiment, the communication subsystem 312 may be configured to receive a wireless signal from detector 340. In various embodiments, the signal may be transmitted using a radio-frequency signal. In various embodiments, communication subsystem 312 may also permit communication between IED 308 and other devices (not shown) associated with an electric power system in electric communication with conductors 330, 332, and 334.

A processing subsystem 316 may be configured to process information received from monitored equipment interface 310 and communication subsystem 312. Processing subsystem 316 may operate using any number of processing rates and architectures. Processing subsystem 316 may be configured to perform various algorithms and calculations described herein. Processing subsystem 316 may be embodied as a general-purpose integrated circuit, an application-specific integrated circuit, a field-programmable gate array, and/or any other suitable programmable logic device.

As discussed above, the processing subsystem 316 may be configured to operate in one or more modes. The processing subsystem 316 may select, or may be used to select, a first mode (e.g., a normal operational mode, a high security mode, or high confidence mode) where data from the detector 340 (e.g., data relating to motion of the conductor 334) is required to be verified before a trip command is sent to the protective action subsystem 314. For example, where conductor 334 motion is detected by the detector 340 and passed to the processing subsystem 316 via the communication subsystem 312, the processing subsystem 316 may require verification by analyzing additional data provided via the communication subsystem 312 or via another source (e.g., data relating to another property related to the conductor 334, such as a current measurement in the conductor 334). In such an embodiment, if a threshold current level is also detected, the processing subsystem 316 may have enough certainty that a fault is present and may send a trip command to the protective action subsystem 314.

The processing subsystem 316 may select, or may be used to select, a second mode (e.g., a fire prevention mode) where data from the detector 340 (e.g., data relating to motion of the conductor 334) is not required to be verified before a trip command is sent to the protective action subsystem 314. Rather, threshold data relating to the one or more environmental conditions (e.g., as discussed above) may instruct the controller to bypass any verification acts and immediately trip the protective action subsystem 314. In some embodiments, threshold data relating to the one or more environmental conditions may automatically place the processing subsystem 316 in the fire prevention mode. In additional embodiments, the processing subsystem 316 may query the data relating to the one or more environmental conditions when a threshold event is received from the detector 340 such that the processing subsystem 316 can decide which operation mode is appropriate and automatically take action or signal an operator to verify a proposed action. In some embodiments, processing subsystem 316 may implement method 200, illustrated in FIG. 2.

Protective action subsystem 314 may be configured to implement an appropriate protective action based on information from monitored equipment interface 310 and communication subsystem 312. For example, protective action subsystem 314 may be configured to interrupt the flow of electric current through conductors 330, 332, and 334 based on a signal from detector 340 that conductor 334 is faulty. Upon receipt of a signal that a conductor is faulty, protective action subsystem 314 may cause monitored equipment interface 310 to interrupt the flow of electric current through conductors 330, 332, and 334. In some embodiments, current interrupting devices 302, 304, and 306 may be actuated by the protective action subsystem 314. In other embodiments, the protective action subsystem 314 may block or suppress automatic reclosing of current interrupting devices 302, 304, and 306.

Location subsystem 318 may be configured to associate the detector 340 with a particular location. In the illustrated embodiment, only a single detector 340 is illustrated for simplicity; however, in other embodiments, a large number of detectors may be placed (e.g., distributed) throughout an electric power system. A location subsystem 318 may be configured to associate each detector with a specific location. Identifying the location of a fault on the electric conductor is the first step in repairing the conductor. Accordingly, location subsystem 318 may help to increase the efficiency of locating and repairing a faulted conductor.

Detector 340 may include a communication subsystem 342, a power supply 344, an electrical sensor 346, an environmental sensor 350, a commissioning subsystem 352, and a processing subsystem 356. A bus 348 may connect the internal elements of detector 340. The communication subsystem 342 may be configured to provide a signal when a fault is detected in the conductor 334.

The power supply 344 may be configured to provide power to detector 340. In some embodiments, power supply 344 may be configured to draw power from conductor 334. In some embodiments, power supply 344 may use a current transformer to harvest energy from conductor 334.

The electrical sensor 346 may be configured to detect a fault in the conductor 334 (e.g., by detecting a property related to the conductor 334, such as motion, electric transmission properties, etc.). In some embodiments, electrical sensor 346 may comprise a current transformer that monitors current flowing through conductor 334. Further, in some embodiments, the same current transformer may be used by power supply 334 to draw power from conductor 334.

The environmental sensor 350 may be used to detect environmental conductions near detector 340. For example, the environmental sensor 350 may comprise a humidity sensor, a temperature sensor, a barometric pressure sensor, a wind sensor, etc. Information about environmental conditions may be transmitted by detector 340 to IED 308 using communication subsystem 342

The commissioning subsystem 352 may be configured to determine whether the detector 340 is operating within established parameters. In some embodiments, the commissioning subsystem 352 is configured to permit a user to establish various thresholds that may be used, along with measurements from sensor 346, to determine when conductor 334 is damaged, broken, or downed.

The processing subsystem 356 may be configured to use information from sensor 346 and commissioning subsystem 352 to determine whether conductor 334 is faulty. The processing subsystem 356 may generate a signal to be transmitted to IED 308 by communication subsystem 342 indicating that conductor 334 is damaged, broken, or downed.

While specific embodiments and applications of the disclosure have been illustrated and described, it is to be understood that the disclosure is not limited to the specific configurations and components disclosed herein. Accordingly, many changes may be made to the details of the above-described embodiments without departing from the underlying principles of this disclosure. The scope of the present disclosure should, therefore, be determined only by the following claims.

What is claimed is:

1. A system to mitigate risk of fire caused by an electric power system, the system comprising: an intelligent electronic device (IED), comprising: a communication subsystem to receive a signal from at least one sensor associated with an electric conductor and related to a condition of the electric conductor; and a processing subsystem in communication with the communication subsystem, the processing subsystem to: operate in at least two modes comprising a high security mode and a fire prevention mode; determine whether the high security mode or the fire prevention mode is selected based on at least one condition external to the electric power system comprising at least one environmental condition proximate to the electric conductor including at least one of a detected level of relative humidity, a detected wind speed, or a detected temperature; when the fire prevention mode is determined to be selected based on the at least one condition external to the electric power system, interrupt a flow of electric current based only on the signal from the at least one sensor associated with the electric conductor; and when the high security mode is determined to be selected based on the at least one condition external to the electric power system, interrupt a flow of electric current based on the signal from the at least one sensor associated with the electric conductor and based on a second condition relating to the electric conductor.

2. The system of claim 1, wherein the at least one sensor associated with the electric conductor comprises a detector to sense motion of the electric conductor exceeding a threshold level and the at least one sensor transmits the signal based on the motion of the electric conductor exceeding the threshold level.

3. The system of claim 2, wherein the at least one sensor comprises at least one of an acceleration sensor or a rotational positional sensor.

4. The system of claim 1, wherein the second condition comprises detection of a traveling wave in the electric conductor.

5. The system of claim 1, wherein the second condition comprises a current level in the electric conductor exceeding a threshold level.

6. The system of claim 1, wherein the processing subsystem is adapted to receive data relating to the at least one environmental condition proximate to the electric conductor and base the interruption of the flow of electric current on the at least one environmental condition.

7. The system of claim 6, wherein the processing subsystem is adapted to receive the at least one environmental condition from the at least one sensor.

8. The system of claim 1, wherein the processing subsystem is adapted to block an automatic reclose scheme in the fire prevention mode.

9. A system to mitigate risk of fire caused by an electric power system, the system comprising: at least one sensor associated with the electric conductor and comprising a first communication subsystem configured to transmit a signal from the at least one sensor relating to a condition of the electric conductor; and an intelligent electronic device (IED), comprising: a second communication subsystem for receiving the signal from the at least one sensor; and a processing subsystem in communication with the second communication subsystem, the processing subsystem to: receive data relating to an environmental condition external to the electric power system and to select one of a fire prevention mode and a high security mode based on the environmental condition, the environmental condition comprising at least one of a detected level of relative humidity, a detected wind speed, a detected temperature, or a fuel load; when the fire prevention mode is selected, interrupt a flow of electric current based on the signal from the at least one sensor associated with the electric conductor; and when the high security mode is selected, interrupt a flow of electric current based on the signal from the at least one sensor associated with the electric conductor and based on a second condition relating to the electric conductor.

10. The system of claim 9, wherein the at least one sensor associated with the electric conductor comprises a detector to detect a break in the electric conductor and the at least one sensor adapted to transmit the signal based on the break in the electric conductor.

11. The system of claim 9, wherein the at least one sensor associated with the electric conductor comprises a detector to sense motion of the electric conductor exceeding a threshold level and the at least one sensor is adapted to transmit the signal based on the motion of the electric conductor exceeding the threshold level.

12. The system of claim 9, wherein the threshold environmental condition comprises a relative humidity.

13. The system of claim 9, wherein the second condition comprises a change in current level in the electric conductor.

14. The system of claim 9, wherein the processing subsystem is adapted to block an automatic reclose scheme in the fire prevention mode.

15. A method to mitigate risk of fire caused by an electric power system, the method comprising: receiving data relating to an electric conductor from at least one sensor associated with the electric conductor; selecting a fire prevention mode or a high security mode prior to detection of a fault in the electric power system, comprising: entering into the fire prevention mode when a threshold environmental condition proximate the electric conductor is verified, the threshold environmental condition comprising at least one of a detected level of relative humidity, a detected wind speed, a detected temperature, or a fuel load; and entering into the high security mode when the control system is not in the fire prevention mode; in the fire prevention mode: receiving the data from the at least one sensor associated with the electric conductor; and interrupting a flow of electric current based on the data from the at least one sensor; and in the high security mode: receiving the data from the at least one sensor associated with the electric conductor; verifying a second condition relating to the electric conductor; and interrupting a flow of electric current based on the data from the at least one sensor and based on the second condition relating to the electric conductor.

16. The method of claim 15, further comprising automatically entering into the fire prevention mode based on the environmental condition proximate to the electric conductor.

17. The method of claim 15, wherein receiving the data relating to the electric conductor comprises detecting motion of the electric conductor.

18. The method of claim 15, wherein the second condition comprises detection of a traveling wave in the electric conductor.

19. The method of claim 15, further comprising blocking an automatic reclose scheme in the fire prevention mode.

* * * * *